United States Patent
Jones et al.

(10) Patent No.: US 9,855,720 B2
(45) Date of Patent: Jan. 2, 2018

(54) UNIDIRECTIONAL OPACITY WATERMARK

(71) Applicant: MorphoTrust USA, LLC, Billerica, MA (US)

(72) Inventors: Robert Jones, Andover, MA (US); Joseph Picardi, Jamaica Plain, MA (US); Dennis Mailloux, Westminster, MA (US)

(73) Assignee: MorphoTrust USA, LLC, Billerica, MA (US)

( * ) Notice: Subject to any disclaimer, the term of this patent is extended or adjusted under 35 U.S.C. 154(b) by 9 days.

(21) Appl. No.: 14/494,102

(22) Filed: Sep. 23, 2014

(65) Prior Publication Data

US 2015/0085285 A1    Mar. 26, 2015

Related U.S. Application Data

(60) Provisional application No. 61/881,230, filed on Sep. 23, 2013.

(51) Int. Cl.
  *B42D 25/333* (2014.01)
  *B42D 25/346* (2014.01)
  (Continued)

(52) U.S. Cl.
  CPC .............. *B32B 3/266* (2013.01); *B32B 37/26* (2013.01); *B32B 38/0004* (2013.01);
  (Continued)

(58) Field of Classification Search
  CPC ..... B42D 25/333; B42D 25/346; B42D 25/23
  (Continued)

(56) References Cited

U.S. PATENT DOCUMENTS 3,604,901 A * 9/1971 Morita .................. B42D 25/00
  283/75
3,802,101 A * 4/1974 Scantlin ........... G06K 19/06046
  283/108
(Continued)

FOREIGN PATENT DOCUMENTS

DE        19934434 B4   10/2006
DE     202009011195 U1    2/2010
(Continued)

OTHER PUBLICATIONS

Notification of Transmittal of the International Search Report and the Written Opinion of the International Searching Authority, or the Declaration, dated Feb. 5, 2015 in corresponding International Patent Application No. PCT/US2014/057013, 21 pages.

*Primary Examiner* — Kyle Grabowski
(74) *Attorney, Agent, or Firm* — Fish & Richardson P.C.

(57) ABSTRACT

A laminar assembly including a first optically opaque layer defining a plurality of through-holes, a second optically opaque layer, an optically transparent inner layer between the inner surface of the first optically opaque layer and the inner surface of the second optically opaque layer, and a preprinted layer proximate the outer surface of at least one of the first and second optically opaque layers. The plurality of through-holes is at least partially filled with material from the optically transparent inner layer, and light is visibly transmitted in a single direction through the plurality of through-holes. Unidirectional opacity watermarks defined by the plurality of through-holes in the laminar assembly provide advantageous anti-counterfeiting measures, and are easy to view and authenticate, yet difficult to simulate.

42 Claims, 6 Drawing Sheets

(51) Int. Cl.

| | |
|---|---|
| *B42D 25/23* | (2014.01) |
| *B32B 3/26* | (2006.01) |
| *B32B 37/26* | (2006.01) |
| *B32B 38/00* | (2006.01) |
| *G01N 21/59* | (2006.01) |
| *G06K 19/077* | (2006.01) |
| *G07D 7/12* | (2016.01) |
| *B42D 25/45* | (2014.01) |
| *B42D 25/455* | (2014.01) |
| *B42D 25/351* | (2014.01) |
| *B42D 25/46* | (2014.01) |
| *B42D 25/00* | (2014.01) |
| *G07D 7/00* | (2016.01) |

(52) U.S. Cl.
CPC .......... *B32B 38/0008* (2013.01); *B42D 25/00* (2014.10); *B42D 25/23* (2014.10); *B42D 25/333* (2014.10); *B42D 25/346* (2014.10); *B42D 25/351* (2014.10); *B42D 25/45* (2014.10); *B42D 25/455* (2014.10); *B42D 25/46* (2014.10); *G01N 21/59* (2013.01); *G06K 19/07722* (2013.01); *G06K 19/07749* (2013.01); *G07D 7/0034* (2017.05); *G07D 7/12* (2013.01); *B32B 2250/03* (2013.01); *B32B 2250/05* (2013.01); *B32B 2307/41* (2013.01); *B32B 2310/0843* (2013.01); *B32B 2425/00* (2013.01); *B32B 2519/00* (2013.01); *B42D 2033/22* (2013.01); *B42D 2035/36* (2013.01); *Y10T 156/1062* (2015.01); *Y10T 428/24339* (2015.01)

(58) Field of Classification Search
USPC ........................................................ 283/113
See application file for complete search history.

(56) References Cited

U.S. PATENT DOCUMENTS

| | | | | |
|---|---|---|---|---|
| 5,567,362 | A * | 10/1996 | Grün | B42D 25/00 |
| | | | | 283/108 |
| 6,328,342 | B1 | 12/2001 | Belousov | |
| 8,673,114 | B2 * | 3/2014 | Krul | D21F 1/0063 |
| | | | | 162/109 |
| 8,675,261 | B2 * | 3/2014 | Green | B42D 25/29 |
| | | | | 283/57 |
| 2004/0229022 | A1 * | 11/2004 | Bourdelais | B42D 25/00 |
| | | | | 428/195.1 |
| 2007/0085337 | A1 * | 4/2007 | Endres | B42D 25/00 |
| | | | | 283/81 |
| 2011/0215563 | A1 * | 9/2011 | Rancien | B42D 25/00 |
| | | | | 283/113 |
| 2012/0176652 | A1 * | 7/2012 | Green | B42D 25/382 |
| | | | | 358/3.28 |
| 2012/0187673 | A1 * | 7/2012 | Stewart | B42D 25/29 |
| | | | | 283/72 |
| 2012/0242072 | A1 * | 9/2012 | LeLoarer | G06K 19/07745 |
| | | | | 283/67 |
| 2014/0290367 | A1 * | 10/2014 | Domke | B42D 25/346 |
| | | | | 73/596 |

FOREIGN PATENT DOCUMENTS

| | | | |
|---|---|---|---|
| DE | WO 2013060465 A1 * | 5/2013 | ........... B42D 25/346 |
| WO | WO 2009021738 A1 * | 2/2009 | |
| WO | WO2011020486 A8 | 4/2011 | |
| WO | WO2012177053 A1 | 9/2012 | |

* cited by examiner

UNIDIRECTIONAL OPACITY WATERMARK

CROSS-REFERENCE TO RELATED APPLICATION

This application claims priority to U.S. Provisional Application Ser. No. 61/881,230 entitled "UNIDIRECTIONAL OPACITY WATERMARK" and filed on Sep. 23, 2013, which is incorporated by reference herein in its entirety.

TECHNICAL FIELD

This disclosure is related to unidirectional opacity watermarks in information-bearing laminar assemblies.

BACKGROUND

Forming watermarks in identification cards typically involves printing dark text or a dark image inside an opaque, white core. The process generally includes using two layers of white material, such as poly(vinyl chloride) or a poly(vinyl chloride) composite. In one example, a visual preprint is added on a first side of the first white layer, and the watermark is printed on the opposite side of the first white layer. The first white layer and the second white layer are fused together, with the watermark of the first white layer facing the second white layer, thereby embedding the watermark in the core of the identification card. When the identification card is held up to a strong light, or backlit, the watermark can be viewed through the front of the card and the back of the card.

Other visible markings on the identification card (e.g., images, text, preprinted patterns) are usually opaque and therefore can interfere with viewing the watermark. For the watermark to be visible, the dark text or image is typically selected to have a large area, such that the watermark can be distinguished from the other visible markings on the identification card. Accordingly, edge definition and detail are generally difficult to attain with watermarks formed by this technology.

SUMMARY

The unidirectional opacity watermark described herein is a security feature for information-bearing laminar assemblies. The unidirectional opacity watermark is visible when light is directed to a first side of the laminar assembly, but is not visible when light is directed to a second side of the laminar assembly. The unidirectional opacity watermark is not opaque, and can have edge definition and detail without requiring a large area. As such, the unidirectional opacity watermark provides advantageous anti-counterfeiting measures, and is easy to view and authenticate, yet difficult to simulate.

In a first general aspect, a laminar assembly includes a first optically opaque layer defining a plurality of through-holes, a second optically opaque layer, an optically transparent inner layer between the inner surface of the first optically opaque layer and the inner surface of the second optically opaque layer, and a preprinted layer proximate the outer surface of at least one of the first and second optically opaque layers. The plurality of through-holes is at least partially filled with material from the optically transparent inner layer, and light is visibly transmitted in a single direction through the plurality of through-holes.

In a second general aspect, a laminar assembly having a unidirectional opacity watermark is fabricated by forming a plurality of through-holes in a first optically opaque layer, positioning an optically transparent core layer between the first optically opaque layer and a second optically opaque layer to yield a stack of layers, and heating the stack of layers to fuse the optically transparent core layer between the first optically opaque layer and the second optically opaque layer, thereby yielding a fused assembly. The plurality of through-holes is at least partially filled with material from the optically transparent inner layer, and light is visibly transmitted in a single direction through the plurality of through-holes.

In a third general aspect, authenticating a laminar assembly includes directing light toward a first side of the laminar assembly and visually inspecting a second side of the laminar assembly for a change in opacity of a portion of the second side of the laminar assembly, and directing light toward the second side of the laminar assembly and visually inspecting the first side of the laminar assembly for a change in opacity of a portion of the first side of the laminar assembly, wherein the second side of the laminar assembly is opposite the first side of the laminar assembly. A visibly detectable change in opacity of a portion of the first side of the laminar assembly or a portion of the second side of the laminar assembly, but not both, verifies authenticity of the laminar assembly.

In a fourth general aspect, a method of authenticating a laminar assembly includes directing light toward a first side of the laminar assembly and visually inspecting a second side of the laminar assembly for a change in opacity of a portion of the second side of the laminar assembly, and directing light toward the second side of the laminar assembly and visually inspecting the first side of the laminar assembly for a change in opacity of a portion of the first side of the laminar assembly, wherein the second side of the laminar assembly is opposite the first side of the laminar assembly. A visibly detectable change in opacity of a portion of the first side of the laminar assembly that differs in shape or position from a visibly detectable change in opacity of a portion of the second side of the laminar assembly verifies authenticity of the laminar assembly.

Implementations of one or more of the above general aspects may independently include one or more of the following features.

The preprinted layer is proximate the outer surface of the first optically opaque layer.

The preprinted layer includes fixed or variable data or images or any combination thereof.

The plurality of through-holes extends through the preprinted layer.

The plurality of through-holes is arranged in the form of one or more fixed or variable images, shapes, designs, textual groupings, or any combination thereof.

At least some of the plurality of through-holes are conical, frustoconical, or a combination thereof.

The area of the opening of at least some of the through-holes at the inner surface of the first optically opaque layer exceeds the area of the opening of the through-holes at the outer surface of the first optically opaque layer.

The area of the opening of at least some of the through-holes at the outer surface of the first optically opaque layer exceeds the area of the opening of the through-holes at the inner surface of the first optically opaque layer.

At least some of the plurality of through-holes are cylindrical.

The diameter of the opening of at least some of the through-holes at the outer surface of the first optically opaque layer, the inner surface of the first optically opaque layer, or both are in a range between 2 mil and 20 mil, or in a range between 4 mil and 10 mil.

A longitudinal axis of at least some of the plurality of through-holes is perpendicular to the outer surface of the first optically opaque layer.

A longitudinal axis of at least some of the plurality of through-holes is arranged at an angle between 45° and 90° with respect to the outer surface of the first optically opaque layer.

A longitudinal axis of at least some of the plurality of through-holes is perpendicular to the outer surface of the first optically opaque layer.

The optically transparent inner layer is an information-bearing layer.

The optically transparent inner layer includes an electronic device, such as a microchip or UHF inlay.

The plurality of through-holes are at least partially filled with material from the first optically opaque layer.

Light directed toward the outer surface of the second optically opaque layer is transmitted through the plurality of through-holes in the first optically opaque layer, such that an outline formed by the plurality of through-holes is visible through the outer surface of the first optically opaque layer.

Light directed toward the outer surface of the first optically opaque layer is not visibly transmitted through the laminar assembly.

Diffuse or ambient light directed toward the outer surface of the second optically opaque layer is not visibly transmitted through the laminar assembly.

The optically transparent inner layer is colored or colorless.

The optically transparent inner layer includes an ultraviolet fluorescent material or fluorescing IR activated material.

The laminar assembly is an identification card or a security document.

The laminar assembly is a contactless smart card or a window card.

The first optically opaque layer, the second optically opaque layer, the optically transparent inner layer, or any combination thereof comprises polycarbonate, polyester, poly(vinyl chloride), polystyrene, or a combination thereof.

The laminar assembly includes a first optically transparent outer layer proximate the first optically opaque layer, and a second optically transparent outer layer proximate the second optically opaque layer.

The laminar assembly includes 5 to 15 layers.

The first optically transparent outer layer, the second optically transparent outer layer, or any combination thereof comprises polycarbonate.

A thickness of the laminar assembly is in a range between 10 mil and 50 mil.

A thickness of the first optically opaque layer is in a range between 2 mil and 8 mil.

A thickness of the second optically opaque layer is in a range between 2 mil and 8 mil.

A thickness of the optically transparent inner layer is in a range between 8 mil and 14 mil.

A thickness of the first and second optically transparent layers is in a range between 2 mil and 8 mil.

A plurality of through-holes are formed via laser ablation, optionally $CO_2$ laser ablation or YAG laser ablation.

The optically transparent inner layer comprises two or more layers.

The plurality of through-holes is a first plurality of through-holes, the second optically opaque layer comprises a second plurality of through-holes, and light is visibly transmitted in a single direction through the second plurality of through-holes.

The light is visibly transmitted through the second plurality of through-holes in a direction opposite the single direction light is visibly transmitted through the first plurality of through-holes.

Unidirectional opacity watermarks described herein provide advantageous anti-counterfeiting measures. These unidirectional opacity watermarks are easy to view and authenticate, yet difficult to simulate.

The details of one or more disclosed implementations are set forth in the accompanying drawings and the description below. Other features, aspects, and advantages will become apparent from the description, the drawings, and the claims.

DETAILED DESCRIPTION

The unidirectional opacity watermark described herein is a security feature for information-bearing laminar assemblies. The unidirectional opacity watermark, in the form of one or more fixed or variable images, shapes, designs, textual groupings, or any combination thereof, is visible when light is directed to a first side of the laminar assembly, but is not visible when light is directed to a second side of the laminar assembly. Information-bearing laminar assemblies include, for example, identification cards, contactless smart cards, "window" cards, passport data pages, and the like. A "fixed" image, shape, design, or textual grouping is generally the same for a multiplicity of laminar assemblies. A "variable" image, shape, design, or textual grouping is generally specific for a subset of laminar assemblies or for a single laminar assembly (e.g., the image, name, signature, birthday, or the like of an individual card bearer).

Figure 1:
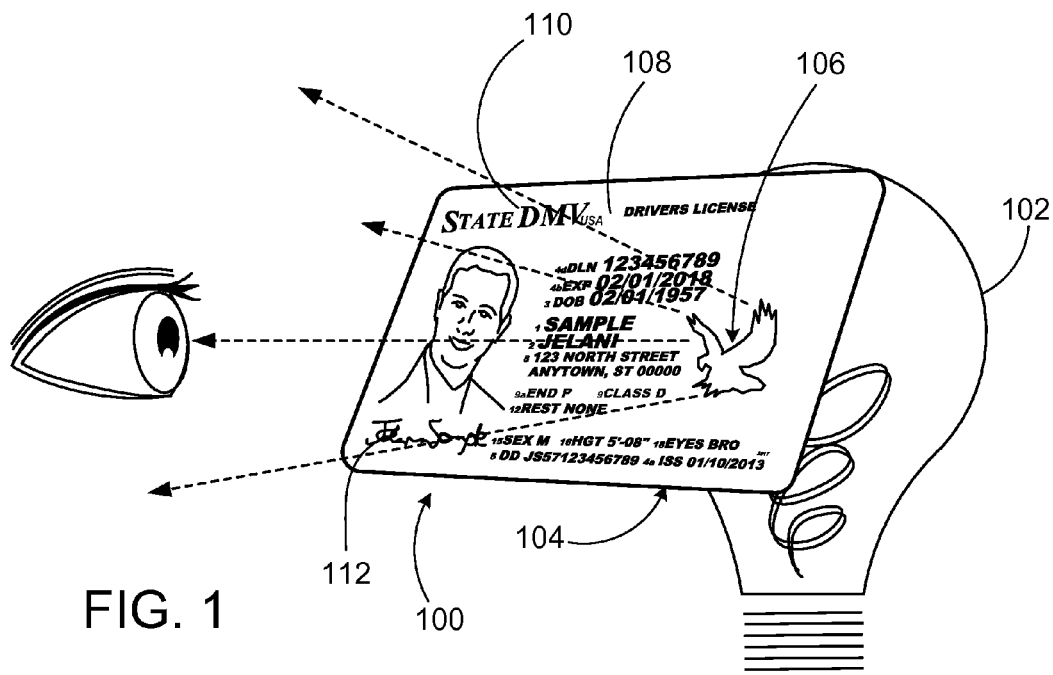
FIG. 1 depicts authentication of an information-bearing laminar assembly with a light source proximate a back side of the information-bearing laminar assembly.

Referring to FIG. 1, identification card 100 is shown as an example of an information-bearing laminar assembly. When light source 102 is positioned proximate first side 104 of identification card 100, unidirectional opacity watermark 106 is visible to the unaided human eye from a second side 108 of the identification card. That is, unidirectional opacity watermark 106 is visible when backlit by a light source proximate (e.g., close to or in contact with) first side 104 of identification card 100, such that light at close range is transmitted through the identification card, making the unidirectional opacity watermark visible via transmission. As depicted in FIG. 1, first side 104 corresponds to the back of identification card 100, and second side 108 corresponds to the front side of the identification card. In other cases, however, the first side 104 corresponds to the front of identification card 100, and the second side 108 corresponds to the back of the identification card. Authentication can be achieved under light (e.g., daytime) or dark (e.g. nighttime) conditions. Suitable light sources for backlighting the unidirectional opacity watermark 106 include, for example, incandescent lights, halogen lights, light-emitting diodes, flashlights, and the like.

As depicted in FIG. 1, the unidirectional opacity watermark 106 is in the form of an image (i.e., an eagle). The color of the unidirectional opacity watermark 106 is influenced by the color of the light from the direct light source 102 and the color of one or more layers in the laminar assembly. In some cases, a layer in the laminar assembly includes a UV fluorescent material that fluoresces when irradiated with a UV light source. In certain cases, a layer in a laminar assembly includes fluorescing IR activated material. Thus, the unidirectional opacity watermark 106 can be white or another color, and is not limited to black or a dark color. The unidirectional opacity watermark 106, typically in the form of one or more fixed or variable images, shapes, designs, textual groupings, or any combination thereof, can be crisp and detailed, and is easily seen (e.g., as light shining through the identification card) against the preprint 110 or variable printing 112 on the identification card 100.

Figure 2:
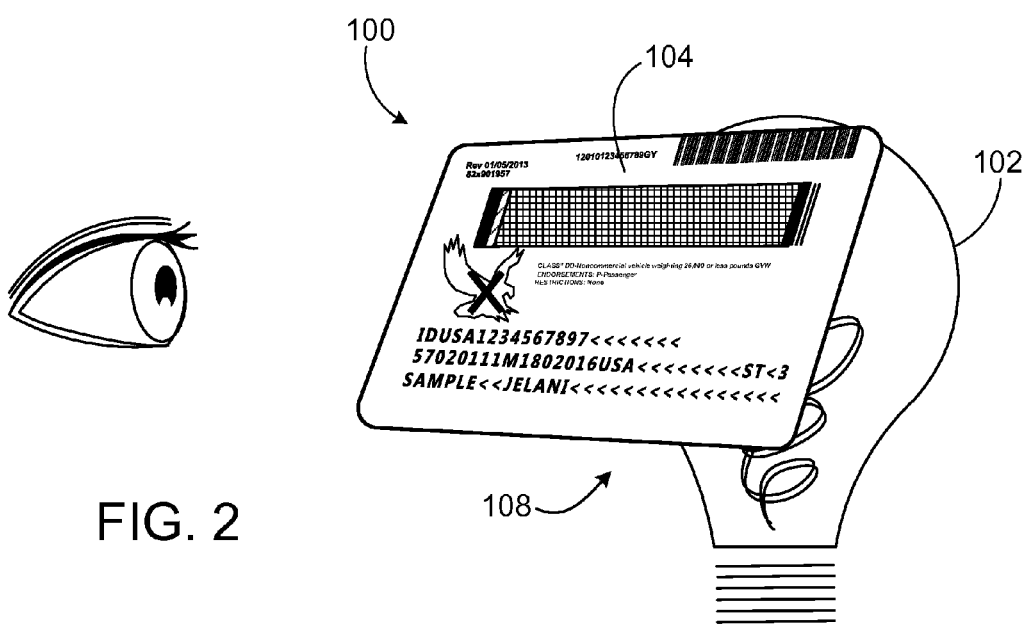
FIG. 2 depicts a unidirectional feature of a unidirectional opacity watermark.

The unidirectional opacity watermark is not visible through the first side 104 of identification card 100 when direct light source 102 is positioned proximate the second side 108 of the identification card. In FIG. 2, the "X" indicates that the unidirectional opacity watermark is not visible from the first side 104 of the identification card 100. That is, neither the "X" nor the unidirectional opacity watermark is visible from the first side 104 of the identification card 100 when the second side 108 of the identification card is backlit. FIG. 2, however, shows where the opacity watermark would appear if it were visible from both sides of the identification card.

Figure 3:
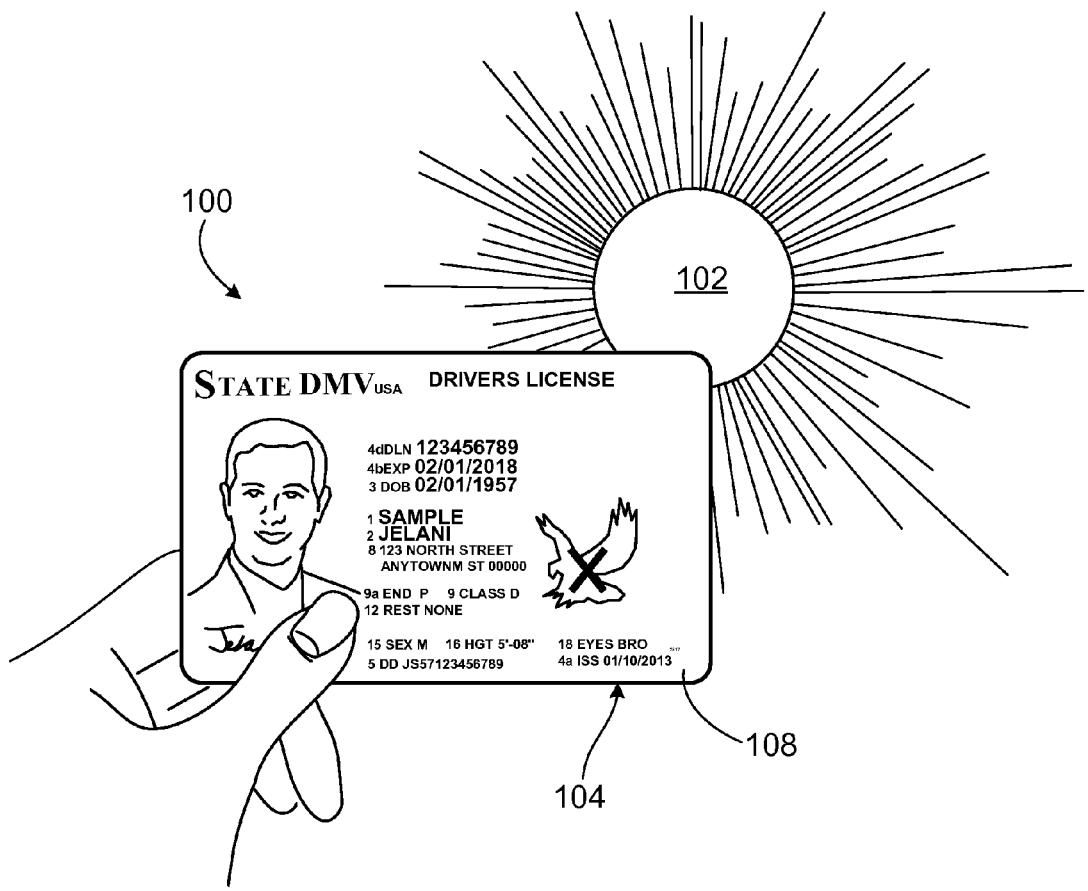
FIG. 3 depicts the behavior of a unidirectional opacity watermark in ambient light.

Unidirectional opacity watermark 106 is not visible through the second side 108 of the identification card 100 when the light source 102 is an ambient light source, such as the sun. Similarly, unidirectional opacity watermark 106 is not visible in ambient interior lighting, such as incandescent or fluorescent lighting, when the light source is not proximate the first side 104 of the identification card 100. In FIG. 3, the "X" indicates that the unidirectional opacity watermark is not visible from the second side 108 of the identification card 100. That is, neither the "X" nor the unidirectional opacity watermark is visible from the second side 108 of the identification card 100 in the presence of ambient (i.e., no direct) light. FIG. 3, however, shows where the opacity watermark would appear if it were visible from the second side 108 under ambient light.

Figure 4:
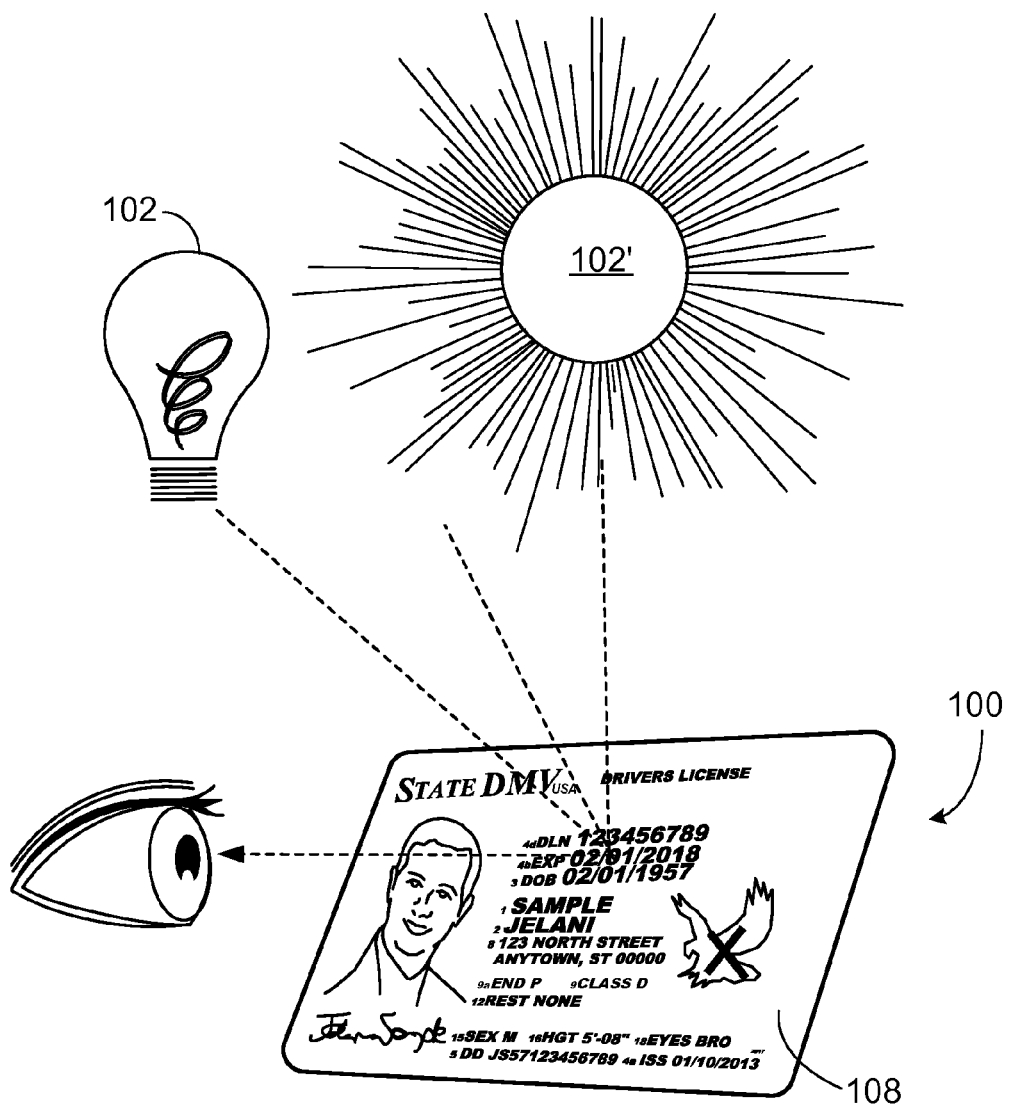
FIG. 4 depicts the behavior of a unidirectional opacity watermark in reflected light.

FIG. 4 depicts identification card 100 in the presence of light sources 102 and 102'. The unidirectional opacity watermark is not visible in the presence of reflected light from light sources 102 and 102'. In FIG. 4, the "X" indicates that the unidirectional opacity watermark is not visible with ambient light reflecting on the second side 108 of the identification card 100. That is, neither the "X" nor the unidirectional opacity watermark is visible from the second side 108 of the identification card 100 in the presence of ambient light reflecting on the second side 108 of the identification card 100. FIG. 4, however, shows where the opacity watermark would appear if it were visible from the second side 108 in reflected light.

Thus, as described with respect to FIGS. 1-4, a unidirectional opacity watermark can be created such that it is visible from the front of a laminar assembly when the back of the laminar assembly is backlit, but not visible from the back of the laminar assembly when the front of the laminar assembly is backlit. Similarly, a unidirectional opacity watermark can be created such that it is visible from the back of a laminar assembly when the front of the laminar assembly is backlit, but not visible from the front of the laminar assembly when the back of the laminar assembly is backlit. In some cases, the unidirectional opacity watermark is an image, as depicted in FIGS. 1-4. In certain cases, the unidirectional opacity watermark includes one or more fixed or variable images, shapes, designs, textual groupings, or any combination thereof. In some instances, the unidirectional opacity watermark may include information specific to the bearer (e.g., variable information such as name, birthdate, image, or the like) or information specific to the origin of type of laminar assembly (e.g., fixed information such as a state seal or flag, concentric circles, words or phrases, or the like). A unidirectional opacity watermark may overlap variable information, fixed information or both. In FIGS. 1-4, however, the unidirectional opacity watermark is not depicted as overlapping variable or fixed information for simplicity.

FIGS. 5A-5D depict examples of unidirectional laminar assemblies 500, 530, 540, and 550, respectively. The layers and materials of these laminar assemblies are generally described with respect to laminar assembly 500 depicted in FIG. 5A

Figure 5A:
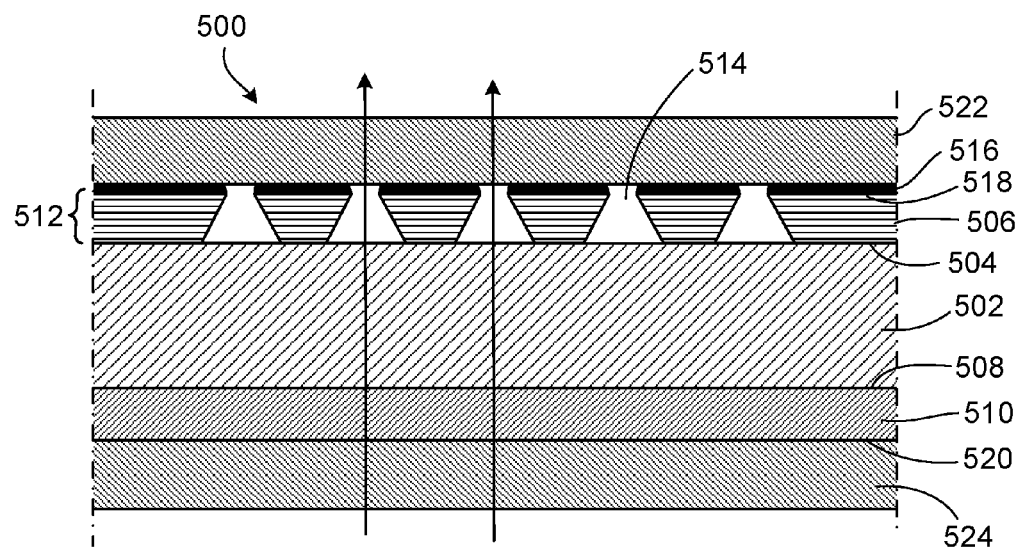
FIGS. 5A-5D depict cross-sectional views of laminar assemblies having unidirectional opacity watermarks.
Figure 5B:
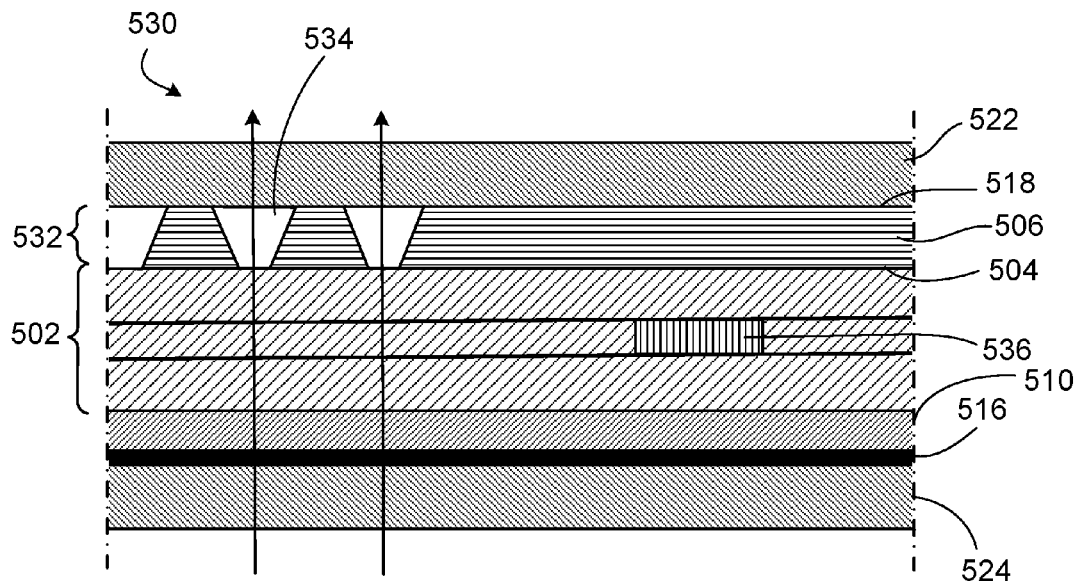

FIG. 5A depicts a cross-sectional view of a portion of a laminar assembly 500 including a unidirectional opacity watermark. Laminar assembly 500 includes optically transparent inner layer 502 between inner surface 504 of first optically opaque layer 506 and inner surface 508 of second optically opaque layer 510. In some cases, optically transparent inner layer 502 includes two or more fused layers (e.g., as depicted in FIG. 5B). In certain cases, a microchip, UHF inlay, or other electronic information-bearing device is embedded in optically transparent inner layer 502 (e.g., as depicted in FIG. 5B). Unidirectional watermark 512 is defined by a plurality of through-holes 514 in first optically opaque layer 506. At least one of first optically opaque layer 506 and second optically opaque layer 510 typically includes a preprinted layer 516 proximate (e.g., printed on) outer surface 518 or 520 of first optically opaque layer 506 or second optically opaque layer 510, respectively. Preprinted layer 516 may include, for example, fixed or variable data or images. As depicted in FIG. 5A, preprinted layer 516 is proximate outer surface 518 of first optically opaque layer 506. Laminar assembly 500 may also include first optically transparent layer 522 and second optically transparent layer 524 proximate first optically opaque layer 506 and second optically opaque layer 510, respectively.

A thickness of laminar assembly 500 is typically in a range between 10 mil and 50 mil. A thickness of first optically opaque layer 506 is typically in a range between 4 mil and 8 mil. A thickness of the second optically opaque layer 510 is typically in a range between 2 mil and 6 mil. A thickness of the optically transparent inner layer 502 is typically in a range between 8 mil and 14 mil. A thickness of the first and second optically transparent layers 522 and 524 is typically in a range between 4 mil and 8 mil. In one example, first and second optically transparent layers 522 and 524 are 6 mil thick, first optically opaque layer 506 is 6 mil thick, second optically opaque layer 510 is 4 mil thick, and optically transparent inner layer 502 is 11 mil thick. Other embodiments may include additional layers, layers with different thicknesses, or a combination thereof.

Layers of laminar assembly 500 are typically formed of polymeric material, such as polycarbonate, polyester, poly (vinyl chloride), polystyrene, or other material known in the construction of identification credentials. In one example, first and second optically transparent layers 522 and 524 are formed of clear polycarbonate LE. In another example, first optically opaque layer 506 is formed of white polycarbonate. First optically opaque layer 506 may have preprinted layer 516 on outer surface 518. In yet another example, second optically opaque layer 510 is formed of white polycarbonate. Various types of polycarbonate are available, for example, from Saudi Basic Industries Corporation (Sabic). Optically transparent inner layer 502 may be formed of clear polycarbonate housing a UHF inlay, such as that available from ASK (Burlington, Vt.).

The through-holes are typically formed via laser ablation (e.g., with a $CO_2$ or YAG laser) of first optically opaque layer 506 before layers of laminar assembly 500 are positioned proximate each other to form the assembly. Forming a pattern of laser-ablated microholes in identification cards is described in U.S. Pat. No. 6,752,432 and U.S. Pat. No. 7,086,666, both of which are incorporated herein by reference. In some cases, the laser on-time ranges from 200 ms to 500 ms at a variety of power settings. When preprinted layer 516 is on outer surface 518 of first optically opaque layer 506, the through-holes are typically formed through preprinted layer 516 and extend through the entire thickness of the first optically opaque layer 506. The through-holes are arranged in the form of one or more fixed or variable images, shapes, designs, textual groupings, or any combination thereof. In one example, the center-to-center distance between through-holes may be about 10 mil. This distance may vary, however, based on equipment, desired effect, diameter of through-holes, or arrangement of through-holes. With respect to FIGS. 1-4, the through-holes are arranged to form the outline of an eagle.

As depicted in FIG. 5A, through-holes 514 are conical (e.g., frustoconical, or having the shape of a frustrum), with the diameter (or area) of the opening at the inner surface 504 of the first optically opaque layer 506 exceeding the diameter (or area) of the opening at the outer surface 518 of the first optically opaque layer. In some cases, the diameter of the opening at the outer surface 518 is in a range of 2 mil to 20 mil or 4 mil to 10 mil, or 5% to 50% (e.g., 10% to 40% or 20% to 30%) of the diameter at the opening of the inner surface 504.

In certain cases, as depicted in FIG. 5B, the diameter (or area) of the opening of the through-holes 534 defining unidirectional watermark 532 at the outer surface 518 of the first optically opaque 506 layer exceeds the diameter (or area) of the opening of the through-holes at the inner surface 504 of the first optically opaque layer 506. The diameter of the opening at the inner surface 504 may be in a range of 2 mil to 20 mil or 4 mil to 10 mil, or 5% to 50% (e.g., 10% to 40% or 20% to 30%) of the diameter at the opening of the outer surface 518. FIG. 5B also depicts multi-layer optically transparent inner layer 502' with electronic device 536 embedded in one layer of the optically transparent inner layer. Electronic device 536 may be, for example, a microchip, UHF inlay, or other electronic information-bearing device.

Figure 5C:
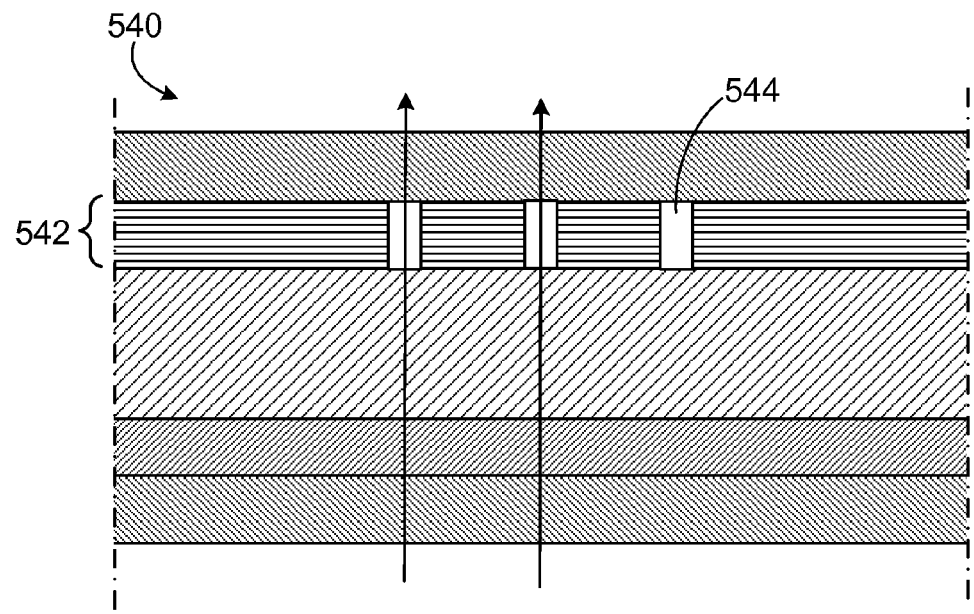

As depicted in FIG. 5C, through-holes 544 of unidirectional watermark 542 of laminar assembly 540 are cylindrical, with a diameter in a range between 2 mil and 20 mil. It should be noted that when preprinted layer 516 is on outer surface 518 of first optically opaque layer 506, it is desirable for the through-holes to have an area at the outer surface such that openings in the preprinted layer are not visible to the human eye, and the preprinted layer does not appear to be perforated.

Figure 5D:
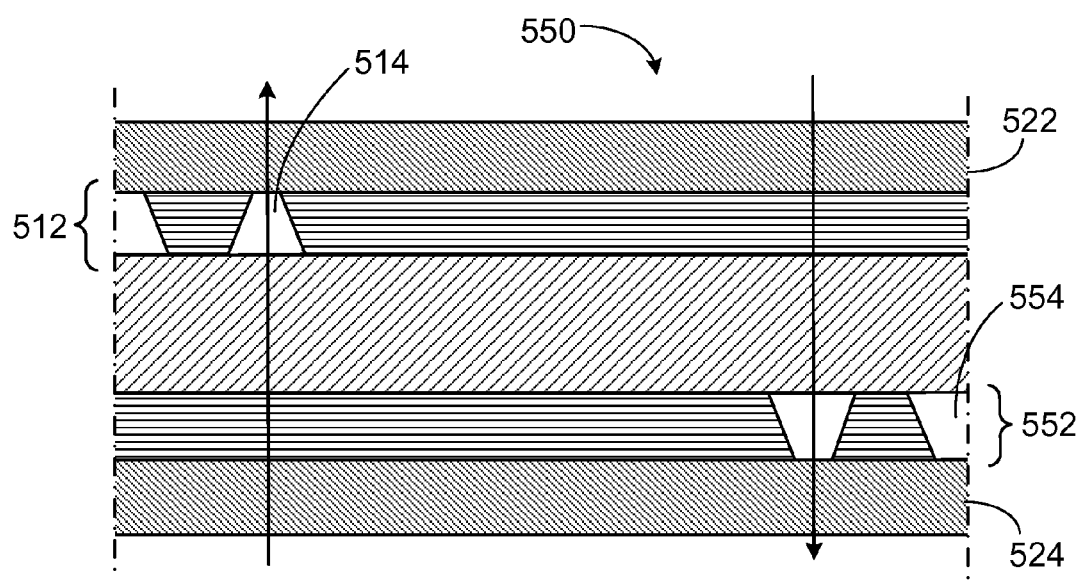

In some embodiments, as depicted in FIG. 5D, laminar assembly 550 includes unidirectional opacity watermarks having opposite directionality, so that a first unidirectional watermark 512 defined by through-holes 514 is visible through first optically transparent outer layer 522 when second transparent outer layer 524 is directly illuminated with a light source, and a second unidirectional watermark 552 defined by through-holes 554 is visible through second transparent outer layer 524 when first transparent outer layer 522 is directly illuminated with a light source. First unidirectional watermark 512 and second unidirectional opacity watermark 552 may be spatially separated from one another and may include different images, shapes, designs, or textual groupings.

In some cases, as depicted in FIGS. 5A-5D, a longitudinal axis of the through-holes is perpendicular to the outer surface of the first optically opaque layer 506. In other cases, a longitudinal axis of the through-holes is arranged at an angle between 45° and 90° with respect to the outer surface of the first optically opaque layer 506. In certain cases, through-holes in a unidirectional opacity watermark may have different sizes, shapes, and/or angular orientations with respect to the surface of the identification card. In various embodiments, the unidirectional opacity watermark is positioned to overlay or avoid certain fixed or variable preprinted items of the laminar assembly, or to avoid an embedded electronic device.

With respect to FIG. 5A, but generally applicable other embodiments, after through-holes 514 are formed in first optically opaque layer 506, layers of laminar assembly 500 are aligned and fused together by processes generally known in the art. During fusing, material from optically transparent inner layer 502 and material from first optically opaque layer 506 fills or at least partially fills through-holes 514. Thus, through-holes 514 are at least partially filled with a mixture of optically transparent (clear) and optically opaque (white) material, yielding lens-like structures. Thus, when a light source is placed proximate the laminar assembly and travels in the direction of the arrows shown in FIGS. 5A-5D, the light is effectively focused by the lens-like structures and is therefore visible at the first optically transparent outer layer 522. However, when light travels in the direction opposite to that indicated by the arrows in FIGS. 5A-5D, light is dispersed in optically transparent inner layer 502, and is not visible at the second optically transparent outer layer 524. Thus, what appears as a small illuminated (e.g., white) hole at the first optically transparent outer layer when the laminar assembly is directly illuminated at the second optically transparent outer layer, is a larger, diffuse white area that is not visible at the second optically transparent outer layer when the laminar assembly is directly illuminated at the first optically transparent outer layer.

Figure 6:
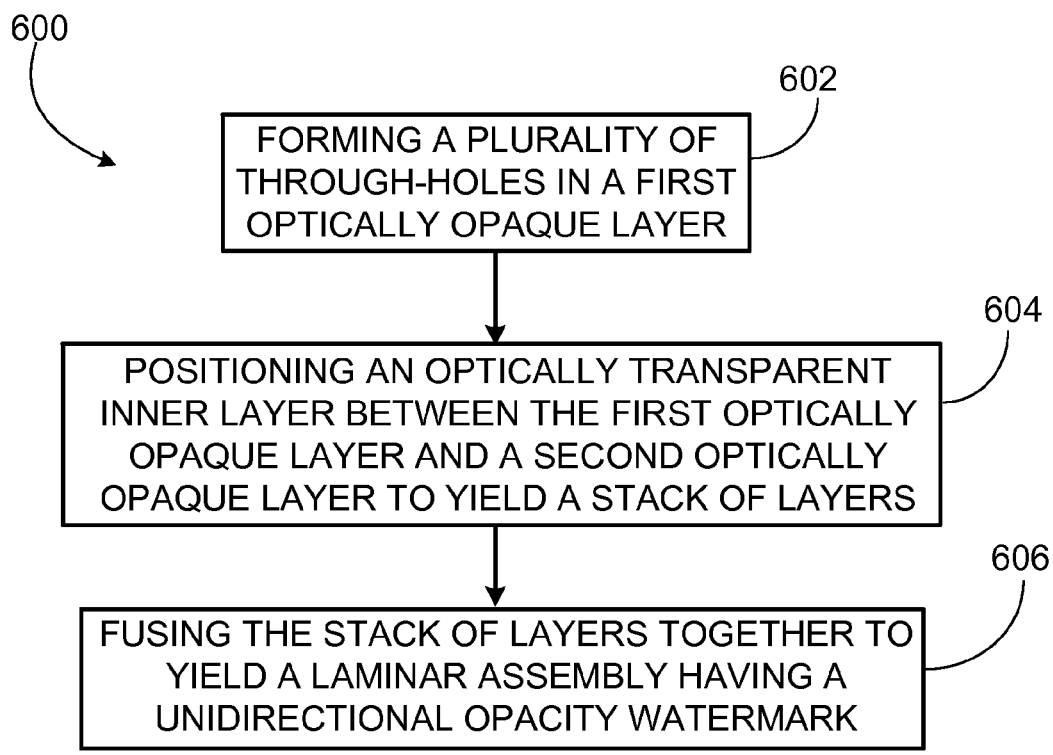
FIG. 6 is a flowchart for a process for forming a laminar assembly with a unidirectional opacity watermark.

FIG. 6 is a flowchart showing process 600 for forming a laminar assembly having a unidirectional opacity watermark. In 602, a plurality of through-holes is formed in a first optically opaque layer. In 604, an optically transparent inner layer is positioned between the first optically opaque layer and a second optically opaque layer to yield a stack of layers. In 606, the stack of layers is heated to fuse the optically transparent core layer between the first optically opaque layer and the second optically opaque layer, thereby yielding a laminar assembly including a unidirectional opacity watermark. In various embodiments, the stack of layers includes additional layers (e.g., up 15 layers) that are fused together. Additional layers may include, for example, laser sensitized clear polycarbonate, clear polycarbonate CORELAM, and the like. In some cases, a laser sensitized polycarbonate layer may be interposed between the first or second optically opaque layer the first or second optically transparent layer, respectively. A thickness of the laser sensitized polycarbonate layer may be in a range between 1 mil and 6 mil (e.g., 2 mil or 4 mil). In implementations having laser sensitized polycarbonate layers, the first or second optically transparent layer may have a thickness in a range between 1 mil and 5 mil (e.g., 2 mil).

EXAMPLE

In one example, a laminar assembly with a unidirectional opacity watermark includes seven layers of polycarbonate, in the following order: 2 mil clear polycarbonate, 4 mil laser sensitized clear polycarbonate, 6 mil white printed polycarbonate into which the conical-shaped through-holes were laser-ablated; 12 mil clear polycarbonate CORELAM, 4 mil white polycarbonate, 2 mil laser sensitized clear polycarbonate, and 2 mil clear polycarbonate.

Material for each layer was cut into 11 by 11.75 inch pieces. The layers were stacked in the sequence described above. Highly polished steel mirror plates were placed on opposite sides of the card material stack (i.e., contacting the 2 mil clear polycarbonate on each side). The material stack and plates were placed on the lower platen of a Tetrahedron Lab Press. The press cycle was initiated after closing the press. The press cycle consists of 3 steps which are executed automatically once the press is closed. The press cycle or process recipe is shown in Table 1.

TABLE 1

Process recipe.

|  | Temperature (° F.) | Pressure (psi) | Dwell time |
| --- | --- | --- | --- |
| Step 1 | 315 | 16 | 30 sec |
| Step 2 | 360 | 370 | 5 min |
| Step 3 | 80 | 370 | 1 min |

Once the press were closed, the platen heaters were turned on and the platens were heated to the specified temperature of each step. If the temperature needed to decrease as in Step 3, water was circulated through the platens. The platen pressure was also increased to the level specified in the process step. Once the specified values of temperature and pressure were reached, the process was held at that level for the amount of time specified as dwell time for that step. On completion of the dwell time, the next step was initiated until the last process step was executed and reached and the specified dwell time has expired.

On completion of the final process step, the pressure went to zero, causing the lower platen to descend to the starting or open position. The material and mirror plate package were removed from the press. The mirror plates were then removed from the fused polycarbonate material stack. The fused material stack was then cut into 15 ID1 sized cards, each containing a unidirectional opacity watermark feature.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description.

What is claimed is:

1. A laminar assembly comprising:
    a first optically opaque layer defining a plurality of through-holes, wherein the first optically opaque layer comprises a polymeric material;
    a second optically opaque layer;
    an optically transparent inner layer between the inner surface of the first optically opaque layer and the inner surface of the second optically opaque layer, and
    a preprinted layer proximate the outer surface of at least one of the first and second optically opaque layers,
    wherein the plurality of through-holes is at least partially filled with material from the optically transparent inner layer, and light is visibly transmitted in a single direction through the plurality of through-holes, and
    wherein light directed toward the outer surface of the first optically opaque layer is not visibly transmitted through the laminar assembly, and light directed toward the outer surface of the second optically opaque layer is transmitted through the plurality of through-holes in the first optically opaque layer, such that an outline formed by the plurality of through-holes is visible through the outer surface of the first optically opaque layer.

2. The laminar assembly of claim 1, wherein the preprinted layer is proximate the outer surface of the first optically opaque layer.

3. The laminar assembly of claim 2, wherein the preprinted layer comprises fixed or variable data or images or any combination thereof.

4. The laminar assembly of claim 2, wherein the plurality of through-holes extends through the preprinted layer.

5. The laminar assembly of claim 1, wherein the plurality of through-holes is arranged in the form of one or more fixed or variable images, shapes, designs, textual groupings, or any combination thereof.

6. The laminar assembly of claim 1, wherein at least some of the plurality of through-holes are conical.

7. The laminar assembly of claim 1, wherein at least some of the plurality of through-holes are frustoconical.

8. The laminar assembly of claim 1, wherein the area of the opening of at least some of the plurality of through-holes at the inner surface of the first optically opaque layer exceeds the area of the opening of the through-holes at the outer surface of the first optically opaque layer.

9. The laminar assembly of claim 1, wherein the area of the opening of at least some of the plurality through-holes at the outer surface of the first optically opaque layer exceeds the area of the opening of the through-holes at the inner surface of the first optically opaque layer.

10. The laminar assembly of claim 1, wherein at least some of the plurality of through-holes are cylindrical.

11. The laminar assembly of claim 1, wherein the diameter of the opening of at least some of the plurality of through-holes at the outer surface of the first optically opaque layer, the inner surface of the first optically opaque layer, or both are in a range between 2 mil and 20 mil, or in a range between 4 mil and 10 mil.

12. The laminar assembly of claim 1, wherein a longitudinal axis of at least some of the plurality through-holes is perpendicular to the outer surface of the first optically opaque layer.

13. The laminar assembly of claim 1, wherein a longitudinal axis of at least some of the plurality of through-holes is arranged at an angle between 45° and 90° with respect to the outer surface of the first optically opaque layer.

14. The laminar assembly of claim 1, wherein a longitudinal axis of at least some of the plurality of through-holes is perpendicular to the outer surface of the first optically opaque layer.

15. The laminar assembly of claim 1, wherein the optically transparent inner layer is an information-bearing layer.

16. The laminar assembly of claim 15, wherein the optically transparent inner layer comprises a microchip or UHF inlay.

17. The laminar assembly of claim 1, wherein at least some of the plurality of through-holes are partially filled with material from the first optically opaque layer.

18. The laminar assembly of claim 1, wherein diffuse or ambient light directed toward the outer surface of the second optically opaque layer is not visibly transmitted through the laminar assembly.

19. The laminar assembly of claim 1, wherein the optically transparent inner layer is colored or colorless.

20. The laminar assembly of claim 1, wherein the optically transparent inner layer comprises an ultraviolet fluorescent material or fluorescing IR activated material.

21. The laminar assembly of claim 1, wherein the laminar assembly is an identification card or a security document.

22. The laminar assembly of claim 1, wherein the laminar assembly is a contactless smart card or a window card.

23. The laminar assembly of claim 1, wherein the first optically opaque layer, the second optically opaque layer, the optically transparent inner layer, or any combination thereof comprises polycarbonate, polyester, poly(vinyl chloride), polystyrene, or a combination thereof.

24. The laminar assembly of claim 1, further comprising:
a first optically transparent outer layer proximate the first optically opaque layer; and
a second optically transparent outer layer proximate the second optically opaque layer.

25. The laminar assembly of claim 24, wherein the first optically transparent outer layer, the second optically transparent outer layer, or any combination thereof comprises polycarbonate.

26. The laminar assembly of claim 24, wherein a thickness of the first and second optically transparent layers is in a range between 2 mil and 8 mil.

27. The laminar assembly of claim 1, wherein a thickness of the laminar assembly is in a range between 10 mil and 50 mil.

28. The laminar assembly of claim 1, wherein a thickness of the first optically opaque layer is in a range between 2 mil and 8 mil.

29. The laminar assembly of claim 1, wherein a thickness of the second optically opaque layer is in a range between 2 mil and 8 mil.

30. The laminar assembly of claim 1, wherein a thickness of the optically transparent inner layer is in a range between 8 mil and 14 mil.

31. The laminar assembly of claim 1, wherein the plurality of through-holes is formed via laser ablation.

32. The laminar assembly of claim 1, wherein the optically transparent inner layer comprises two or more layers.

33. The laminar assembly of claim 1, wherein the plurality of through-holes is a first plurality of through-holes, the second optically opaque layer comprises a second plurality of through-holes, and light is visibly transmitted in a single direction through the second plurality of through-holes.

34. The laminar assembly of claim 33, wherein light is visibly transmitted through the second plurality of through-holes in a direction opposite the single direction light is visibly transmitted through the first plurality of through-holes.

35. The laminar assembly of claim 1, wherein the first optically opaque layer comprises a plastic.

36. The laminar assembly of claim 35, wherein the first optically opaque layer comprises polycarbonate, polyester, poly(vinyl chloride), polystyrene, or a combination thereof.

37. A method of forming a laminar assembly, the method comprising:
forming a watermark comprising plurality of through-holes in a first optically opaque layer, wherein the first optically opaque layer comprises a polymeric material;
positioning an optically transparent core layer between the first optically opaque layer and a second optically opaque layer to yield a stack of layers; and
heating the stack of layers to fuse the optically transparent core layer between the first optically opaque layer and the second optically opaque layer, thereby yielding a fused assembly,
wherein the fused assembly comprises a preprinted layer proximate the outer surface of at least one of the first and second optically opaque layers,
wherein some of the through-holes are at least partially filled with material from the optically transparent inner layer, and light is visibly transmitted in a single direction through the plurality of through-holes, and
wherein light directed toward the outer surface of the first optically opaque layer is not visibly transmitted through the laminar assembly, and light directed toward the outer surface of the second optically opaque layer is transmitted through the plurality of through-holes in the first optically opaque layer, such that an outline formed by the plurality of through-holes is visible through the outer surface of the first optically opaque layer.

38. The method of claim 37, wherein at least some of the plurality of through-holes are conical, frustoconical, or cylindrical.

39. A laminar assembly comprising:
a first optically opaque layer defining a plurality of through-holes, wherein the first optically opaque layer comprises a polymeric material;
a second optically opaque layer;
an optically transparent inner layer between the inner surface of the first optically opaque layer and the inner surface of the second optically opaque layer, and
a preprinted layer proximate the outer surface of at least one of the first and second optically opaque layers,
wherein the plurality of through-holes is at least partially filled with material from the optically transparent inner layer, and light is visibly transmitted in a single direction through the plurality of through-holes, and
wherein diffuse or ambient light directed toward the outer surface of the second optically opaque layer is not visibly transmitted through the laminar assembly, and light directed toward the outer surface of the second optically opaque layer is transmitted through the plurality of through-holes in the first optically opaque layer, such that an outline formed by the plurality of through-holes is visible through the outer surface of the first optically opaque layer.

40. The laminar assembly of claim 39, wherein the plurality of through-holes is arranged in the form of one or more fixed or variable images, shapes, designs, textual groupings, or any combination thereof.

41. The laminar assembly of claim 39, wherein at least some of the plurality of through-holes are conical or frustoconical.

42. The laminar assembly of claim 39, wherein the laminar assembly is an identification card, a security document, a contactless smart card, or a window card.

* * * * *

UNITED STATES PATENT AND TRADEMARK OFFICE
CERTIFICATE OF CORRECTION

PATENT NO. : 9,855,720 B2
APPLICATION NO. : 14/494102
DATED : January 2, 2018
INVENTOR(S) : Robert L. Jones, Joseph Picardi and Dennis Mailloux Page 1 of 1

It is certified that error appears in the above-identified patent and that said Letters Patent is hereby corrected as shown below:

In the Claims

Column 10, Line 48, in Claim 9, after "plurality", insert -- of --.

Column 10, Line 61, in Claim 12, after "plurality", insert -- of --.

Signed and Sealed this
Twelfth Day of June, 2018

Andrei Iancu
*Director of the United States Patent and Trademark Office*